United States Patent [19]

Goldman et al.

[11] Patent Number: 5,061,259

[45] Date of Patent: Oct. 29, 1991

[54] ABSORBENT STRUCTURES WITH GELLING AGENT AND ABSORBENT ARTICLES CONTAINING SUCH STRUCTURES

[75] Inventors: Stephen A. Goldman, Wyoming; James C. Horney; Herbert L. Retzsch, both of Cincinnati, all of Ohio

[73] Assignee: The Procter & Gamble Company, Cincinnati, Ohio

[21] Appl. No.: 616,162

[22] Filed: Nov. 20, 1990

Related U.S. Application Data

[63] Continuation of Ser. No. 529,017, May 25, 1990, abandoned, which is a continuation of Ser. No. 455,772, Dec. 28, 1989, abandoned, which is a continuation of Ser. No. 146,904, Jan. 22, 1988, abandoned, which is a continuation-in-part of Ser. No. 87,137, Aug. 19, 1987, abandoned.

[51] Int. Cl.⁵ .............................................. A61F 13/12
[52] U.S. Cl. .................................. 604/368; 604/370; 604/374
[58] Field of Search ............... 604/358, 364, 365, 367, 604/368, 371, 372, 374, 378–382, 385.1, 385.2

[56] References Cited

U.S. PATENT DOCUMENTS

| | | | |
|---|---|---|---|
| 3,670,731 | 6/1972 | Harmon | 128/284 |
| 3,901,236 | 8/1975 | Assarsson et al. | 128/284 |
| 3,971,373 | 7/1976 | Braun | 128/146.2 |
| 4,102,340 | 7/1978 | Mesek et al. | 128/287 |
| 4,103,058 | 7/1978 | Humlicek | 428/171 |
| 4,105,033 | 8/1978 | Chatterjee et al. | 128/285 |
| 4,145,464 | 3/1979 | McConnell et al. | 428/171 |
| 4,340,556 | 7/1982 | Ciencewicki | 264/119 |
| 4,373,519 | 2/1983 | Errede et al. | 128/156 |
| 4,381,782 | 5/1983 | Mazurak et al. | 604/368 |
| 4,389,513 | 6/1983 | Miyazaki | 525/186 |
| 4,401,795 | 8/1983 | Herman et al. | 525/327.8 |
| 4,429,001 | 1/1984 | Kolpin et al. | 428/283 |
| 4,460,642 | 7/1984 | Errede et al. | 428/283 |
| 4,535,098 | 8/1985 | Evani et al. | 521/149 |

(List continued on next page.)

FOREIGN PATENT DOCUMENTS

| | | |
|---|---|---|
| 156649 | 10/1985 | European Pat. Off. |
| 198683 | 10/1986 | European Pat. Off. |
| 216147 | 4/1987 | European Pat. Off. |
| 318989 | 6/1989 | European Pat. Off. |
| 339461 | 11/1989 | European Pat. Off. |
| 349240 | 1/1990 | European Pat. Off. |
| 349241 | 1/1990 | European Pat. Off. |
| 54-157788 | 12/1979 | Japan . |
| 56-65630 | 6/1981 | Japan . |
| 57-82104 | 1/1982 | Japan . |
| 86/62463 | 3/1986 | Japan . |
| 86/106151 | 5/1986 | Japan . |
| 1500559 | 2/1978 | United Kingdom . |

OTHER PUBLICATIONS

Sanyo Chem. Ind., "Superabsorbent Polymer–SANWET IM-300/SANWET IM-1000", (1982).
Nippon Shokubai Kagaku Kogyo K.K., "AQUALIC CA", Stockhausen Inc., FAVOR SAB-901 (1983).
BASF AG., "LUQUASORB HC 9/80—Superabsorbent Based on Polyacrylic Acid or Aqueous Fluids".

Primary Examiner—Randall L. Green
Assistant Examiner—K. M. Reichle
Attorney, Agent, or Firm—George W. Allen; Jerry J. Yetter

[57] ABSTRACT

The present invention relates to absorbent structures and absorbent gelling agent compositions suitable for use in disposable absorbent articles such as diapers, incontinence products and catamenial products. The absorbent structures comprise hydrophilic fiber material and nonfragile particles of polymeric gelling agent. The gelling agent particles incorporated into such structures are selected to have a mass median particle size ranging from about 400 to 700 microns, with the amounts of very large and very small particles kept below certain minimum concentrations. Absorbent structures utilizing gelling agent particles of such particle size characteristics possess unexpectedly high absorbent capacities and the gelling agent therein can be utilized very efficiently and effectively.

20 Claims, 1 Drawing Sheet

U. S. PATENT DOCUMENTS

| | | | |
|---|---|---|---|
| 4,551,191 | 11/1985 | Kock et al. | 156/276 |
| 4,552,938 | 11/1985 | Mikita et al. | 526/240 |
| 4,578,068 | 3/1986 | Kramer et al. | 604/368 |
| 4,587,308 | 5/1986 | Makita et al. | 525/373 |
| 4,604,313 | 8/1986 | McFarland et al. | 428/172 |
| 4,610,678 | 9/1986 | Weisman et al. | 604/368 |
| 4,625,001 | 11/1986 | Tsubakimoto et al. | 526/88 |
| 4,645,789 | 2/1987 | Dabi | 524/379 |
| 4,654,039 | 3/1987 | Brandt et al. | 604/368 |
| 4,657,537 | 4/1987 | Zimmerer | 604/360 |
| 4,666,975 | 5/1987 | Yamasaki et al. | 524/733 |
| 4,666,983 | 5/1987 | Tsubakimoto et al. | 525/119 |
| 4,673,402 | 6/1987 | Weisman et al. | 604/368 |
| 4,685,909 | 8/1987 | Berg et al. | 604/360 |
| 4,685,915 | 8/1987 | Hasse et al. | 604/378 |
| 4,699,823 | 10/1987 | Kellenberger et al. | 428/219 |

ABSORBENT STRUCTURES WITH GELLING AGENT AND ABSORBENT ARTICLES CONTAINING SUCH STRUCTURES

CROSS REFERENCE TO RELATED APPLICATIONS

This application is a continuation of the abandoned U.S. application having Ser. No. 529,017, filed May 25, 1990, which is in turn a continuation of the abandoned application having Ser. No. 455,772, filed Dec. 28, 1989, which in turn is a continuation of the abandoned U.S. application having Ser. No. 146,904, filed January 22, 1988, which is in turn a continuation-in-part of the abandoned U.S. application having Ser. No. 087,137, filed Aug. 19, 1987, all of which applications were filed in the names of Stephen A. Goldman, James C. Horney and Herbert L. Retzsch.

BACKGROUND OF THE INVENTION

The present invention relates to fibrous web structures suitable for absorbing discharged body fluids and to absorbent gelling agent compositions especially useful in these structures. Such structures can be incorporated into disposable absorbent articles such as sanitary napkins, infant diapers, adult incontinence pads and the like.

Absorbent structures which comprise entangled masses of fibers, i.e., fibrous webs, are well known in the art. Such structures can imbibe liquids, such as discharged body fluids, both by an absorption mechanism wherein fluid is taken up by the fiber material itself and by a wicking mechanism wherein fluid is acquired by, distributed through and stored in the capillary interstices between fibers. One means for improving the absorbency characteristics of such fibrous web structures is to incorporate therein so-called superabsorbent polymers which imbibe fluid to thereby form a swollen hydrogel material. The resulting hydrogel serves to retain fluid such as discharged body liquids within the structure. An absorbent structure of this type wherein hydrogel-forming materials in particulate (including fiber) form are incorporated into fibrous webs is disclosed in Weisman and Goldman; U.S. Pat. No. 4,610,678; issued Sept. 9, 1986.

The size and configuration of particle-form hydrogel-forming polymers (i.e., gelling agents) incorporated into absorbent structures can vary widely. The above-cited U.S. Pat. No. 4,610,678, for example, indicates that gelling agent particles incorporated into such absorbent structures can range in size from about 30 microns to about 4 mm. In actual commercial practice, however, the particles of gelling agent employed in absorbent cores for disposable diapers are frequently irregular but not highly elongated in configuration, range in particle size from about 45 to 850 microns and have a mass median particle size of from about 200 to 370 microns. Particles of this shape and size are generally selected because of industrial hygiene and ease-of-processing considerations.

Some commercially available gelling agent materials are furthermore produced in the form of particles which are agglomerates of smaller particles since the larger agglomerates are easier to handle in gelling agent synthesis and packaging operations. It is believed, however, that agglomerates of this type break down to some degree during their incorporation into disposable absorbent articles manufactured in commercial operations and during subsequent use of such articles. Products of this type such as diapers thus may actually contain gelling agent in the form of particles that are somewhat smaller than the gelling agent agglomerates originally provided in raw material form for diaper-making operations.

Whatever the size and form of gelling agent particles employed in known absorbent structures, the gelling agent is generally more expensive than the staple fiber component which forms the principal part of the structure. Accordingly, the materials, configurations and processing used in making such absorbent structures are often manipulated and adjusted in order to maximize the absorbent capacity of the absorbent structure and the effective absorbent capacity of the gelling agent material employed in the structure. In this manner, the minimum amount of gelling agent consistent with the realization of desired absorbent performance objectives can be used. This, in turn, tends to minimize the cost of producing the absorbent structure.

Given the fact that there is a continuing need to improve absorbent structure absorbency characteristics, it is an objective of the present invention to provide a type of absorbent structure configuration wherein structure absorbent capacity and effective capacity of the gelling agents therein can be improved.

It is a further object of this invention to provide such absorbent structures of improved absorbent capacity and gelling agent efficiency by the simple adjustment and control of particle size distribution of the gelling agent materials employed in the absorbent structure.

It is a further object of the present invention to provide gelling agent compositions which have controlled particle size characteristics and which are especially suitable for incorporation into such absorbent structures.

It is a further object of the present invention to provide disposable absorbent articles such as diapers, training pants, incontinence pads, sanitary napkins and the like, which utilize such absorbent structures of improved absorbency characteristics to form their absorbent cores.

SUMMARY OF THE INVENTION

In one of its embodiments, the present invention is directed to a specific type of absorbent structure suitable for use in disposable absorbent articles. Such structures comprise a web formed from a combination of from about 40% to 95% by weight of the structure of hydrophilic fibers and from about 5% to 60% by weight of the structure of nonfibrous, nonfragile particles of hydrogel-forming polymeric gelling agent. This polymeric gelling agent has an equilibrium gel volume of at least about 20 grams of synthetic urine per gram of gelling agent. Furthermore, these gelling agent particles have a particle size distribution such that the particles have a mass median particle size of from about 400 to 700 microns. No more than about 16% by weight of these particles should have a particle size less than 200 microns and no more than about 16% by weight of these particles should have a particle size greater than 1000 microns. The gelling agent particles themselves are thoroughly dispersed among the hydrophilic fibers forming the web. The resulting web structure has a density ranging from about 0.06 g/cm$^3$ to 0.3 g/cm$^3$.

In another of its embodiments, the present invention is directed to absorbent gelling agent compositions especially suitable for use in fibrous absorbent web structures. Such compositions comprise a plurality of nonfibrous, nonfragile particles of gelling agent material wherein this plurality of particles has the same particle size characteristics as the particles incorporated into the absorbent structures hereinbefore described. The gelling agent material used to form these particles comprises from about 50 to 99.999 mole percent of polymerized, unsaturated polymerizable acid group-containing monomers and from about 0.001 to 5 mole percent of a crosslinking agent. Such gelling agent material is partially neutralized, has a degree of neutralization of at least about 50% and has a gel volume of at least about 20 grams of synthetic urine per gram of gelling agent material.

In yet another of its embodiments, the present invention is directed to absorbent articles of improved absorbency characteristics. Such articles comprise a liquid impervious backing sheet, a liquid pervious topsheet and an absorbent core positioned between the backing sheet and the topsheet. The absorbent core comprises an absorbent web structure of the same type as hereinbefore described.

DETAILED DESCRIPTION OF THE INVENTION

The absorbent structures of the present invention are webs or batts which contain both fibrous and nonfibrous components, and the gelling agent compositions of the present invention contain only nonfibrous components. For purposes of this invention, the terms "fibers" and "fibrous" refer to a specific type of "particulate" material wherein the length to diameter ratio of such particulate material is greater than about 10. "Nonfibrous" particles, conversely, are those wherein the length to diameter ratio is about 10 or less.

In the first of its several embodiments, the present invention relates to absorbent structures which comprise fibrous webs containing nonfibrous particles of absorbent gelling agent material. The principal component of these absorbent web structures comprises hydrophilic fiber material. For purposes of the present invention, a fiber is "hydrophilic" if water or aqueous body fluid readily spreads on or over the surface of the fiber (without regard to whether or not the fiber actually imbibes fluid or forms a gel). The hydrophilic fibers which are employed will generally have an average diameter which ranges from about 1 to 200 microns. More preferably, the average diameter of these hydrophilic fibers will range from about 10 to 100 microns. Substantially all of the hydrophilic fibers incorporated into the structures herein preferably have a fiber length of at least 1 mm.

The type of hydrophilic fiber material is not critical for use in the structures of the present invention. Any type of hydrophilic fiber which is suitable for use in conventional absorbent products is also suitable for use in the absorbent structures herein. Examples of hydrophilic fiber material include cellulose, modified cellulose, rayon, polyesters such as polyethylene terephthalate (DACRON), hydrophilic nylon (HYDROFIL), and the like.

Suitable hydrophilic fibers also include hydrophobic fibers which have been hydrophilized with a hydrophilizing agent. Such fibers include surfactant-treated or silica-treated thermoplastic fibers derived, for example, from polyolefins such as polyethylene or polypropylene, polyacrylics, polyamides, polystyrenes, polyurethanes and the like. In fact, hydrophilized hydrophobic fibers which are in and of themselves not very absorbent and which, therefore, do not provide webs of sufficient absorbent capacity to be useful in conventional absorbent structures, are suitable for use in the structures of this invention by virtue of their good wicking properties. This is because, in the structures herein, wicking propensity of the fibers is far more important than the absorbent capacity of the fiber material itself.

For reasons of availability and cost, cellulosic fibers are generally preferred for use herein as the hydrophilic fiber component of the web structure. Most preferred are wood pulp fibers.

Other cellulosic fiber materials which may be especially useful in certain absorbent structures herein are the stiffened, twisted, curled, cellulosic fibers which can be produced by internally cross-linking cellulose fibers with a cross-linking agent. Fibers of this general type are disclosed, for example, in Bernardin, U.S. Pat. No. 3,224,926, issued Dec. 21, 1965; Steiger, U.S. Pat. No. 3,241,553, issued Mar. 22, 1966; Chung, U.S. Pat. No. 3,440,135, issued Apr. 22, 1969; Steiger, U.S. Pat. No. 3,658,613, issued Apr. 26, 1972; Chatterjee, U.S. Pat. No. 3,932,209, issued Jan. 13, 1976 and Sangenis et al, U.S. Pat. No. 4,035,147, issued July 12, 1977, all of which patents are incorporated herein by reference.

One especially preferred type of stiffened, twisted, curled cellulose fibers useful as the hydrophilic fiber component of the absorbent web structures herein comprises cellulose fibers which have been internally cross-linked, for example with a $C_2$–$C_8$ dialdehyde, while such fibers are in a relatively dehydrated state. Such fibers can be defined in terms of their dry fiber and wet fiber twist counts (at least 4.5 twist nodes per millimeter dry and at least 0.5 twist nodes per millimeter less than that when wet and preferably also at least about 3.0 twist nodes per millimeter wet) and by their fluid retention characteristics (average isopropyl alcohol retention value of less than 30%; average water retention value of from 28% to 50%). Stiffened, twisted, curled cellulosic fibers of this type are described in greater detail in European Patent Publication No. 251,676; published Jan. 7, 1988 and in European Patent Publication No. 252,650; published Jan. 13, 1988. Both of these published patent applications were filed in the name of The Procter & Gamble Company and both are incorporated herein by reference.

The hydrophilic fiber component of the structures herein will generally comprise from about 40% to 95% by weight of the structure, more preferably from about 60% to 95% by weight. Most preferably, the hydrophilic fiber component will comprise from about 70% to 90% by weight of the structure. These concentrations of hydrophilic fiber material include the weight of hydrophilizing agent, if any, employed thereon.

The second essential component of the absorbent structures herein comprises discrete, nonfibrous, nonfragile particles of a particular type of polymeric gelling agent. These polymeric gelling agents are those materials which, upon contact with fluids (i.e., liquids) such as water or body fluids, imbibe such fluids and thereby form hydrogels. In this manner, fluid discharged into the absorbent structures herein can be acquired and held by the particles of the polymeric gelling agent, thereby providing the structures herein with enhanced absorbent capacity and/or improved fluid retention performance.

The polymeric gelling agent particles which are employed will generally comprise a substantially water-insoluble, slightly cross-linked, partially neutralized, hydrogel-forming polymer material. Such polymer materials can be prepared from polymerizable, unsaturated, acid-containing monomers. Thus, such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids and mixtures thereof. Upon polymerization, monomeric units of this type will comprise from about 50 mole percent to 99.999 mole percent, more preferably from about 75 mole percent to 99.99 mole percent of the gelling agent material.

Suitable unsaturated acidic monomers for use in preparing the polymeric gelling agents used in this invention include those listed in Brandt/Goldman/Inglin; U.S. Pat. No. 4,654,039, issued Mar. 31, 1987, and in its allowed reissue application Ser. No. 060,718, filed June 10, 1987, both of which are incorporated herein by reference. Preferred monomers include acrylic acid, methacrylic acid, and 2-acrylamido- 2-methyl propane sulfonic acid. Acrylic acid itself is especially preferred for preparation of the polymeric gelling agent material.

In the hydrogel-forming polymeric gelling agent the polymeric component formed from unsaturated, acid-containing monomers may be grafted on to other types of polymer moieties such as starch or cellulose. Acrylic acid grafted starch materials of this type are also especially preferred for use herein.

Preferred polymer gelling agents which can be prepared from conventional types of monomers include hydrolyzed acrylonitrile grafted starch, acrylic acid grafted starch, polyacrylates, maleic anhydride copolymers and combinations thereof. Especially preferred are the polyacrylates and acrylic acid grafted starch.

Whatever the nature of the basic polymer components of the hydrogel-forming polymeric gelling agents used in the absorbent structures herein, such materials will in general be slightly cross-linked. Cross-linking serves to render the hydrogel- forming polymer gelling agents used in this invention substantially water-insoluble, and cross-linking thus in part determines the gel volume and extractable polymer characteristics of the hydrogels formed from the polymeric gelling agents employed. Suitable cross-linking agents are well known in the art and include, for example, those described in greater detail in Masuda et al; U.S. Pat. No. 4,076,663; issued Feb. 28, 1978, incorporated herein by reference. Preferred cross-linking agents are the di- or polyesters of unsaturated mono- or polycarboxylic acids with polyols, the bisacrylamides and the di- or triallyl amines. Especially preferred cross-linking agents are N,N'-methylenebisacrylamide, trimethylol propane triacrylate and triallyl amine. The cross-linking agent can generally comprise from about 0.001 mole percent to 5 mole percent of the resulting hydrogel-forming polymer material. More preferably, the cross-linking agent will comprise from about 0.01 mole percent to 3 mole percent of the hydrogel-forming polymeric gelling agent used herein.

The slightly cross-linked, hydrogel-forming polymeric gelling agents which may be used in the structures of the present invention are generally employed in their partially neutralized form. For purposes of this invention, such materials are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to herein as the "degree of neutralization." Degree of neutralization will preferably not exceed 98%.

The polymeric gelling agent materials used in the absorbent structures herein must have a relatively high capacity for imbibing fluids encountered in absorbent structures. The absorbent capacity of such materials can be quantified by referencing the "gel volume" of the polymeric gelling agents which are to be selected for use in the present invention.

For purposes of this invention, gel volume can be defined in terms of the amount of synthetic urine absorbed by any given polymeric gelling agent and is specified as grams of synthetic urine per gram of polymeric gelling agent. Gel volume in synthetic urine can be determined by forming a suspension of about 0.1–0.2 parts of dried polymeric gelling agent to be tested with about 20 parts of synthetic urine. This suspension is maintained at ambient temperature under gentle stirring for a time sufficient, e.g., about 1 hour, for swelling equilibrium to be attained. Using a procedure described in greater detail hereinafter in the Test Methods section, the gel volume of the polymeric gelling agent in grams of synthetic urine per gram of polymeric gelling agent is then calculated from the weight fraction of the polymeric gelling agent in the suspension and the ratio of the liquid volume excluded from the formed hydrogel to the total volume of the suspension.

The structures of the present invention, and especially the structures which are to be used in diapers, adult incontinence products or training pants, will generally employ polymeric gelling agents having a gel volume of at least about 20 grams of synthetic urine per gram of polymeric gelling agent. When the structures herein are constructed from cellulosic fibers such as wood pulp fibers, it may be desirable to utilize polymer gelling agent having a somewhat higher gel volume, i.e., a gel volume between about 25 and 60 grams of synthetic urine per gram of gelling agent.

Structures constructed from certain types of cellulosic fiber material such as, for example, the stiffened, twisted, curled cellulosic fibers hereinbefore described may actually be more effective at absorbing fluid if gelling agents of somewhat lower gel volumes are employed. Gelling agent of generally lower gel volume tends to form hydrogels of generally higher gel strength (as quantified by hydrogel shear modulus in the manner described in the hereinbefore-referenced U.S. Pat. No. 4,654,039 and U.S. Reissue Application Ser. No. 060,718). Thus, in structures wherein the hydrophilic fibers are stiffened, twisted, curled cellulose fibers, it may be preferable to employ polymeric gelling agent having a gel volume of from about 20 to 35 grams of synthetic urine per gram of gelling agent.

Another feature of the polymeric gelling agents which are especially useful in the absorbent structures herein relates to the level of extractable polymer material present in such hydrogel-forming material. Extractable polymer levels can be determined by contacting a sample of hydrogel-forming polymeric gelling agent material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The particular procedure used to determine extractable polymer content of the polymeric gelling agents used herein is also set forth in the hereinbefore referenced U.S. Pat. No. 4,654,039 and Reissue Application Ser. No. 060,718. Polymeric gelling agent materials especially useful in the structures herein are those which have an equilibrium extractables content in synthetic urine of no more than about 17%, preferably no more than about 10% by weight of the polymeric gelling agent.

An essential feature of the present invention is the utilization of the above-described polymeric gelling agents in the structures herein in the form of nonfibrous, nonfragile particles having certain particle size characteristics. In particular, it has been discovered that an unexpected improvement in absorbent structure capacity and effective gelling agent capacity within an absorbent structure can be realized by incorporating polymeric gelling agent into such absorbent structures in the form of particles which are generally larger than those which have heretofore been conventionally employed. Generally, provision of gelling agent particles of this relatively larger size requires the use of one or more manufacturing or processing techniques which eliminate or reduce the amount of smaller, finer gelling agent particles which are introduced, along with hydrophilic fiber, into the absorbent structures herein. An upper limit on gelling agent particle size is also provided since gelling agent particles which are too large may be less desirable from a consumer aesthetics standpoint.

Specifically, the present invention requires the utilization in the absorbent structures herein of polymeric gelling agent particles of a selected mass median particle size and preferably a certain particle size deviation from the mass median particle size. For purposes of the present invention, particle size is defined as the dimension of a gelling agent particle which is determined by sieve size analysis. Thus, for example, in principle, a particle that is retained on a sieve with 710 micron openings is considered to have a particle size greater than 710 microns, a particle that passes through a sieve with 710 micron openings and is retained on a sieve with 500 micron openings is considered to have a particle size between 500 and 710 microns, and a particle that passes through a sieve with 500 micron openings is considered to have a particle size less than 500 microns.

Further, for purposes of this invention, the mass median particle size of a given sample or plurality of gelling agent particles is defined as the particle size which divides the sample or plurality in half on a mass basis, i.e., half of the sample or plurality by weight will have a particle size greater than the mass median particle size and half of the sample or plurality by weight will have a particle size less than the mass median particle size. Thus, for example, the mass median particle size of a sample of gelling agent particles is 500 microns if one half of the sample by weight is retained on a sieve with openings of 500 microns. A standard particle-size plotting method (wherein cumulative weight percent of the particle sample retained on or passed through a given sieve size is plotted versus sieve-opening size on probability paper) is typically used to determine mass median particle size when the 50% mass value does not correspond to the size opening of a U.S.A. Standard Testing Sieve. A plot of this type is also typically used to determine the distribution of particle size about the mass median value.

The polymeric gelling agent particles employed in the absorbent structures of this invention must have a mass median particle size within the range of from about 400 to 700 microns with no more than about 16% by weight of these gelling agent particles having a particle size less than 200 microns and no more than about 16% by weight of these particles having a particle size greater than 1000 microns. Preferably, the mass median particle size of the gelling agent particles used in the structures herein will range from about 410 to 650 microns with no more than about 16% by weight of these particles having a particle size less than 210 microns. More preferably, the mass median particle size of the gelling agent particles will range from about 420 to 600 microns with no more than about 16% by weight of the particles having a particle size less than 220 microns and no more than about 16% by weight of the particles having a particle size greater than 900 microns.

Within the foregoing mass median particle size and particle size distribution limitations, it is possible to even further identify preferred particle size characteristics for the gelling agent particles useful herein by means of standard sieve analyses. In a typical sieve analysis, a sample or plurality of gelling agent particles is sifted through a set number of screens of diminishing screen opening size and the weight percent of the sample retained on and/or passing through each screen is determined. Standard methods for making such sieve analyses have been established, for example, by the American Society for Testing Materials (ASTM). One such method employs a Ro-Tap testing sieve shaker (manufactured by W. S. Tyler, Inc.) and a series of screens identified by either U.S. Sieve Series or Tyler Standard Sieve Series designations. Determination of particle size distribution using such a technique is described in greater detail in *Perry's Chemical Engineers' Handbook, Sixth Edition*, (McGraw-Hill Book Company, 1984) at pp. 21-13 to 21-19, which publication is incorporated herein by reference.

Particle size distribution characteristics as determined by a typical 5-screen ASTM standard analysis for preferred and more preferred gelling agent samples of the present invention are set forth as follows:

| Screen Opening Size (Microns) | U.S. Sieve Series Alternate Designation | Tyler Equivalent Designation | Preferred Distribution (Wt. %) | More Preferred Distribution (Wt. %) |
|---|---|---|---|---|
| 1410 | on No. 14 | on 12 mesh | <0.1 | 0–0.05 |
| 1190 | on No. 16 | on 14 mesh | <1.0 | 0–0.5 |
| 841 | on No. 20 | on 20 mesh | 10–35 | 15–25 |
| 297 | on No. 50 | on 48 mesh | >50 | 60–70 |
| 149 | on No. 100 | on 100 mesh | <15 | 10–14 |
| 149 | thru No. 100 | thru 100 | ≦5 | 1–3 |

| Screen Opening Size (Microns) | U.S. Sieve Series Alternate Designation | Tyler Equivalent Designation | Preferred Distribution (Wt. %) | More Preferred Distribution (Wt. %) |
|---|---|---|---|---|
| | | mesh | | |

The polymeric gelling agent particles can be adjusted to, or close to, the requisite particle size distribution by controlling the processing techniques used to prepare the gelling agent. Frequently this will involve varying and monitoring the conditions under which the gelling agent is polymerized, dried, chopped, ground and/or agglomerated. Once gelling agent particles are formed by whatever process, further treatment such as screening may be required to remove particles which, if left in, would cause the gelling agent particle component to fall outside the scope of the hereinbefore-described particle size distribution requirements.

One preferred technique for preparing particles which are larger than those ordinarily prepared by gelling agent polymerization-drying-chopping techniques involves agglomeration of smaller particles to produce larger agglomerates. Agglomeration techniques can thus be used to raise the mass median particle size of gelling agent particles and to thereby provide particles in agglomerated form which are suitable for use in the structures herein. Agglomeration techniques are well known in the art and may or may not involve the use of moisture addition to smaller gelling agent particles or the use of a binder or other type of agglomerating medium.

Gelling agent particles used in the absorbent structures herein, whether or not in agglomerated form, should be nonfragile. For purposes of the present invention, such particles are nonfragile if they are stable enough to withstand the forces encountered in conventional absorbent structure manufacture and/or use without breaking apart and unduly separating into smaller component particles. This means that the gelling agent particles of the invention should be stable enough that they do not break apart into smaller particles to the extent that the resulting aggregation of particles (before swelling) falls outside the scope of the particle size limitations hereinbefore set forth.

Polymeric gelling agent particles having the requisite particle size distribution are incorporated into the absorbent web structures of the present invention in a concentration of from about 5% to 60% by weight of the structure. Use of gelling agent levels below about 5% renders such structures less able to retain aqueous body fluids imbibed by the structure. At higher gelling agent concentrations, for example those above about 60% by weight and even above about 40% by weight, it is believed that the desirable effects of using generally larger gelling agent particles to improve absorbent capacity and effective gelling agent capacity will diminish. Thus, preferably the gelling agent particles will comprise from about 10% to 30% by weight of the absorbent structures herein.

The absorbent structures herein can contain a variety of optional materials in addition to the essential hydrophilic fiber and polymeric gelling agent components. Such optional materials can include, for example, fluid distribution aids, antimicrobials, pH control agents, perfumes, etc. If present, these optional components will generally comprise no more than about 30% by weight of the structures herein.

The absorbent structures herein with their essential hydrophilic fiber and polymeric gelling agent particulate components can be prepared by any process or technique which provides a web comprising a combination of the fibers and the nonfibrous gelling agent particles. Within such a fiber/particle combination, the gelling agent particles should be thoroughly dispersed among the hydrophilic fibers forming the web. For purposes of this invention, gelling agent particles are "thoroughly dispersed" among the hydrophilic fibers if there are no significant instances of individual gelling agent particles being in contact only with each other and not with one or more hydrophilic fibers. Preferably, this will mean that there should be no zones or regions (e.g., zones or regions of cubic centimeter or larger) within the absorbent structure wherein the concentration of gelling agent exceeds the 60% limit set forth hereinbefore.

Within the web structures herein, the particles of the polymeric gelling agent must be thoroughly dispersed but may or may not be uniformly distributed. In particular, there may be regions or zones of the web structures which have higher concentrations of gelling agent particles than do other regions or zones of the structure. In one embodiment of this type, there may be a concentration gradient of gelling agent particles along the thickness dimension of the structure with the lowest concentration of gelling agent being at or near the surface of the structure which receives fluid and the highest concentration of gelling agent being at or near the opposite end of the thickness dimension.

Figure 2:
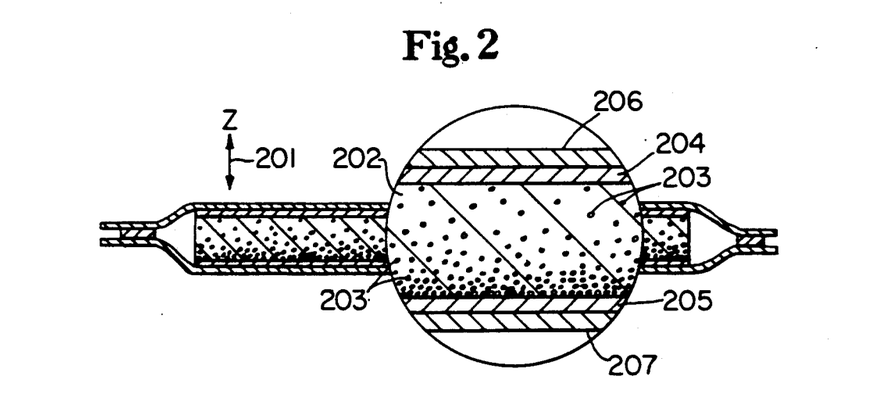
FIG. 2 of the drawing submitted herewith represents a cross-sectional view of an absorbent article wherein the core thereof comprises a structure having a z-direction concentration gradient of gelling agent particles.

A structure of this type is illustrated in FIG. 2 of the drawing which shows a cross section of an absorbent article having a thickness dimension extending substantially in the z-direction 201. The structure comprises a batt 202 of hydrophilic fiber material positioned between an overlying topsheet 206 and an underlying backsheet 207. In this embodiment creped wadding or tissue sheets 204 and 205 are located between the batt 202 and the topsheet 206 and backsheet 207 respectively. Dispersed within the hydrophilic fibers of the batt 202 are particles 203 of polymeric gelling agent. As shown in FIG. 2, there is a concentration gradient of the gelling agent particles 203, in the z-direction within the batt 202 with the highest concentration of particles 203 being nearest the article backsheet 207.

The density of the absorbent structures herein can be of some importance in determining the absorbent properties of the structures and of the absorbent articles in which such structures are employed. The density of the absorbent structures herein will generally be in the range of from about 0.06 to about 0.3 g/cm$^3$, and more preferably within the range of from about 0.09 to about 0.22 g/cm$^3$. Typically the basis weight of the absorbent structures herein can range from about 0.02 to 0.12 gm/cm$^2$.

Density values for these structures are calculated from basis weight and caliper. Caliper is measured under a confining pressure of 0.137 psi (0.94 kPa). Density and basis weight values include the weight of the hydrogel-forming particles. Density of the structures herein need not be uniform throughout the structures. Within the density ranges hereinbefore set forth, structures of this invention can contain regions or zones of relatively higher or relatively lower density.

Absorbent structures of this invention can be formed by air-laying a substantially dry mixture of hydrophilic fibers and polymeric gelling agent particles and, if desired or necessary, densifying the resulting web. Such a procedure is described more fully in Weisman and Goldman; U.S. Pat. No. 4,610,678; issued Sept. 9, 1986, incorporated herein by reference.

As indicated in U.S. Pat. No. 4,610,678, the air-laid webs formed by this procedure will preferably comprise substantially unbonded fibers and will preferably have a moisture content of 10% or less. In preparing webs of this invention by an air-laying process or by any other conventional procedure, care should be taken in handling and transporting the polymeric gelling agent particles so as to avoid breaking these particles down into smaller particles. This is especially true when the gelling agent particles are in an agglomerated form wherein the agglomerates may be more friable than nonagglomerated particles. If the gelling agent particles, e.g., agglomerates, are roughly treated during web structure preparation or thereafter, the particles actually incorporated into the structure (even though such particles are "nonfragile") may not have the requisite particle size distribution characteristics set forth hereinbefore.

In another of its embodiments, the present invention relates to gelling agent compositions per se which are especially suitable for incorporation as absorbents into fibrous absorbent web structures. Such compositions comprise a plurality of nonfibrous, nonfragile particles of polymeric gelling agent material. The gelling agent material itself is of the same type as hereinbefore described in detail. The plurality of gelling agent particles likewise has the same particle size characteristics as hereinbefore set forth for the gelling agent particles which are incorporated into the absorbent structure embodiments of this invention.

In yet another of its embodiments, the present invention relates to absorbent articles which utilize as an essential component an absorbent structure of the type hereinbefore described in detail. By "absorbent article" herein is meant a consumer product which is capable of absorbing significant quantities of water and other fluids (i.e., liquids), like body fluids. Examples of absorbent articles include disposable diapers, sanitary napkins, incontinence pads, paper towels, facial tissues, toilet pads and the like. The absorbent structures of this invention are particularly suitable for use in articles like diapers, incontinence products, and sanitary napkins.

Absorbent articles herein will in general comprise a liquid impervious backing sheet, a liquid pervious, relatively hydrophobic topsheet and an absorbent core comprising an absorbent structure of the present invention positioned between the backing sheet and the topsheet. Liquid impervious backing sheets can comprise any material, for example, polyethylene or polypropylene having a caliper of about 1.5 mils, which will help retain fluid within the absorbent article. Relatively hydrophobic, liquid pervious topsheets can comprise any material such as polyester, polyolefin, rayon and the like which is substantially porous and permits a fluid to readily pass therethrough into the underlying absorbent structure.

Particularly preferred absorbent articles herein are disposable diapers. Disposable diapers comprising the absorbent structures of the present invention may be made by using conventional diaper making techniques, but by replacing or supplementing the wood pulp fiber web ("airfelt") core which is typically used in conventional diapers with an absorbent structure of the present invention. Articles in the form of disposable diapers are fully described in Duncan and Baker, U.S. Pat. No. Re 26,151, issued Jan. 31, 1967; Duncan, U.S. Pat. No. 3,592,194, issued July 13, 1971; Duncan and Gellert, U.S. Pat. No. 3,489,148, issued Jan. 13, 1970; and Buell, U.S. Pat. No. 3,860,003, issued Jan. 14, 1975; which patents are incorporated herein by reference. A preferred disposable diaper for the purpose of this invention comprises an absorbent core containing an absorbent structure of this invention; a topsheet superposed or co-extensive with one face of the core, and a liquid impervious backsheet superposed or co-extensive with the face of the core opposite the face covered by the topsheet. The backsheet most preferably has a width greater than that of the core thereby providing side marginal portions of the backsheet which extend beyond the core. The diaper is preferably constructed in an hourglass configuration.

Figure 1:
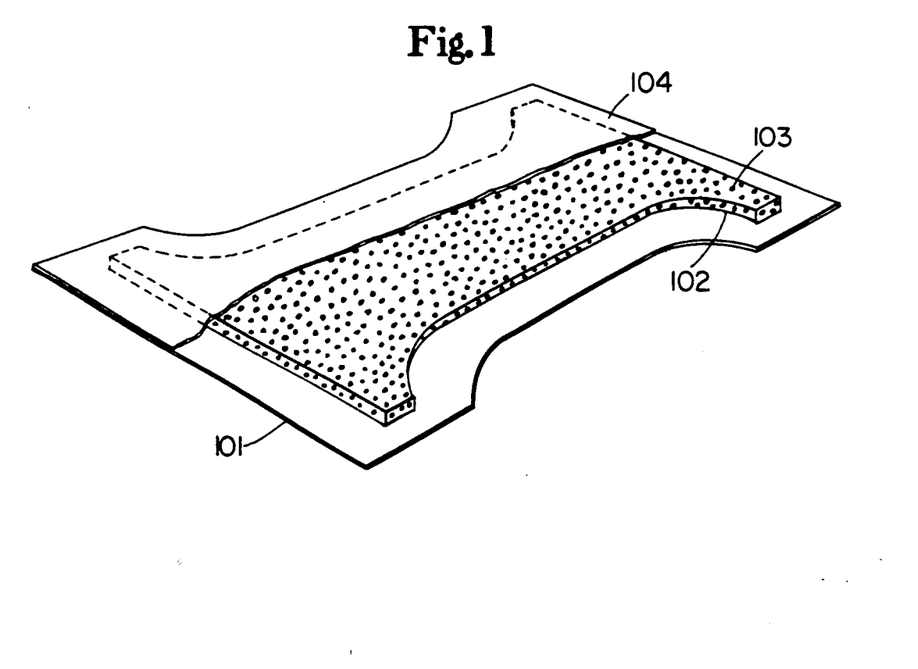
FIG. 1 of the drawing submitted herewith represents a cutaway view of a disposable diaper which is a preferred configuration for the absorbent articles herein.

One embodiment of a disposable diaper article according to the present invention is shown in FIG. 1 of the drawing. The hourglass-shaped diaper structure of Figure comprises a liquid impervious backing sheet 101. Positioned on the top of the backing sheet 101 is an hourglass-shaped absorbent core 102 comprising the absorbent structure of the present invention. This core contains hydrophilic fiber material such as wood pulp fiber. Also distributed throughout the absorbent core 102 are discrete particles 103 of polymeric gelling agent, which particles have the requisite size distribution hereinbefore described. Positioned on top of the hourglass-shaped absorbent core 102 is liquid pervious topsheet 104.

Because the absorbent structures of the present invention have a high absorbent capacity for menstrual fluid as well as for urine, such structures, even though defined in terms of capacity for synthetic urine, are also quite suitable for use in sanitary napkins. As is the case with disposable diapers, sanitary napkins utilizing the present absorbent structures may be derived from conventional sanitary napkins by simply replacing or supplementing the absorbent core thereof (typically a web of wood pulp fibers) with the gelling agent-containing absorbent structure of the present invention. Such replacement may be on a weight-by-weight basis, which results in a reduction in volume and a gain in capacity; or the replacement may be on a less than equal weight basis, thereby sacrificing part of the gain in absorbent capacity in favor of a reduction in bulk. The absorbent structures used in sanitary napkins preferably have a caliper of from about 0.1 mm to about 2 mm, more preferably from about 0.3 mm to about 1 mm.

An example of a sanitary napkin comprises a pad of the absorbent structure of the present invention; a hydrophobic topsheet; and a fluid impervious bottom sheet. The topsheet and the backsheet are placed at opposite sides of the absorbent structure. Optionally, the absorbent structure is wrapped in envelope tissue. Suitable materials for top sheets, bottom sheets and envelope tissue are well known in the art. A more detailed description of sanitary napkins and suitable materials for use therein is found in Duncan and Smith, U.S. Pat. No. 3,871,378; issued Mar. 18, 1975, the disclosure of which is incorporated herein by reference.

TEST METHODS

In describing the present invention in the following examples, certain characteristics of the polymeric gelling agent particles and the absorbent structures containing them are set forth. Where reported, these characteristics can be determined using the following test methods:

Gel Volume of the Gelling Agent

Gel volume in terms of grams of synthetic urine absorbed per gram of polymeric gelling agent is determined by swelling the polymer samples in several aliquots of synthetic urine. The amount of such synthetic urine actually absorbed by the polymeric gelling agent is determined by a procedure which involves use of a synthetic urine solution containing Blue Dextran so that optical absorbance measurements can be used to calculate the amount of synthetic urine that is not taken up by the hydrogel which forms.

a) Blue Dextran Solution Preparation

A 0.03% Blue Dextran (BD) solution is prepared by dissolving 0.3 parts of Blue Dextran (Sigma D-5751) in 1000 parts of Synthetic Urine (SU) solution. Synthetic Urine is 15.0 parts of 1% TRITON X-100, 60.0 parts of NaCl, 1.8 parts of $CaCl_2 \cdot 2H_2O$, and 3.6 parts of $MgCl_2 \cdot 6H_2O$, diluted to 6000 parts with distilled $H_2O$. The resulting solution has an absorbance of about 0.25 at its absorbance maximum of 617 nm.

Hydrogel Equilibration

Aliquots of the hydrogel-forming polymeric gelling agent to be tested are swelled in (i) 20 parts of Synthetic Urine (SU) solution and (ii) 20 parts of Blue Dextran (BD) solution. The suspension in the Blue Dextran (BD) solution is prepared in duplicate. For most hydrogels, 0.1–0.25 parts of hydrogel-forming dried powder is required to give a sufficiently high spectrophotometer reading relative to the Blue Dextran reference solution. One hour of equilibration at ambient temperature under gentle stir-bar stirring is usually sufficient for swelling equilibrium to be attained. After equilibration, a 3 ml aliquot of supernatant is separated from each gel suspension by decantation followed by centrifugation.

c) Gel Volume Determination

The optical absorbency (ABS) of each supernatant is determined spectrophotometrically with an accuracy of 0.001 absorbance units. The Synthetic Urine solution is used as an ABS=0.000 reference. The absorbency of the supernatant from the synthetic urine suspension without Blue Dextran should not exceed 0.01 A; higher values indicate scattering from residual hydrogel gel particles or residual additives, and further centrifugation is necessary. The absorbency of the Blue Dextran supernatants should exceed the absorbency of the Blue Dextran reference solution by at least 0.1 absorbance units. Absorbency values below this range indicate the need to adjust the amount of polymeric gelling agent used to prepare the gel suspension.

d) Gel Volume Calculation

The Gel Volume in synthetic urine of the polymeric gelling agent in gms/gm is calculated from (i) the weight fraction of the polymeric gelling agent in the gel suspension and (ii) the ratio of the excluded volume to the total volume of the suspension. Since Blue Dextran is excluded from the hydrogel due to its high molecular weight, this ratio is related to the measured absorbencies. The following equation is used to calculate the gel volume:

$$\text{Gel Volume} = \left[ \frac{(\text{gms } BD \text{ Solution})}{(\text{gms polymeric gelling agent*})} \right] \times$$

$$\left[ 1 - \frac{(ABS\ BD\ \text{solution})}{(ABS\ BD\ \text{supernatant} - ABS\ SU\ \text{supernatant})} \right]$$

*Corrected to a dry weight basis

Absorbent Structure Density

Reported density measurements are all made under a confining pressure of 9.6 grams/$cm^2$ (0.94 kPa). Measurements are made using a Precision Scientific Penetrometer that is modified for caliper measurements.

Absorbent Capacity of Structure

The absorbent capacity of an absorbent structure can be determined by an equilibrium demand-absorbency test. In such a test, a 5.4 cm diameter sample of the absorbent structure is placed on a 7.5 cm diameter glass frit [Por E (ASTM 4–8 microns) from Ace Glass] that is maintained in fluid contact with a reservoir containing synthetic urine. In this setup, the reservoir is positioned on the pan of a Mettler AE160 Analytical Balance. This provides a continuous readout of the weight of synthetic urine in the reservoir and, by difference, the weight of synthetic urine taken up by the absorbent structure. The height of the frit and the height of the reservoir are adjusted to approximately the same level. A confining weight of 0.2 psi (1.38 kPa) is placed on top of the absorbent structure sample. Using this setup, the number of grams of synthetic urine taken up per gram of structure, once equilibrium is reached, can be determined.

The absorbent structures herein, as well as disposable absorbent articles containing them, are illustrated by the following examples.

EXAMPLE I

An absorbent structure with a basis weight of about 0.072 g/$cm^2$ is prepared by airlaying a substantially uniform mixture of about 80% by weight wood pulp fibers and about 20% by weight of particles of a cross-linked, partially neutralized, sodium polyacrylate gelling agent. The resulting fibrous web is then calendered to form a structure which has a density of about 0.21 g/$cm^3$. The wood pulp fibers employed are southern soft wood slash pine fibers (Foley fluff). The gelling agent has an equilibrium gel volume of about 24 grams of synthetic urine per gram of gelling agent and a degree of neutralization of about 70%.

The particles of gelling agent are screened such that a No. 25/35 fraction is utilized in this absorbent structure. The 25/35 size fraction contains particles that pass through a U.S.A. Standard Testing Sieve with 710 micron openings (No. 25 U.S. Series Alternate Sieve Designation) and are retained on a U.S.A. Standard Testing Sieve with 500 micron openings (No. 35 U.S. Series Alternate Sieve Designation). This particle-size fraction is collected between U.S.A. Standard Testing Sieves (Fisher) after thirty minutes of sieving with a Ro-Tap Sieve Shaker (Tyler).

The absorbent capacity of the structure containing gelling agent particles of this size fraction is determined using the procedure set forth hereinbefore in the Test Methods section and is found to be 11.4 grams of synthetic urine per gram of structure. Since it is known that the equilibrium capacity of a comparable 100% Foley fluff structure at 0.2 psi is about 6.0 g/g, it is possible to calculate an effective absorbent capacity of the gelling agent in the above structure. This is done by determining the capacity differential in grams between the gelling agent-containing structure and a comparable 100% Foley fluff structure and by dividing this difference by the dry weight in grams of the gelling agent. The effective absorbent capacity of the gelling agent determined in this manner thus represents the unit increase in equilibrium capacity of the absorbent structure per unit of added hydrogel-forming polymeric gelling agent. For purposes of this invention a comparable structure without the gelling agent is one which has the same basis weight and density as the Foley fluff component of the gelling agent-containing structure. Such a comparable structure for this Example I has a basis weight of about 0.057 g/cm² and a density of about 0.17 g/cm³. Using this procedure for the Example I structure, the effective absorbent capacity of the gelling agent in the structure is calculated to be 33.0 grams of synthetic urine per gram of gelling agent.

EXAMPLE II

Absorbent structures similar to that of Example I with approximately the same concentration of gelling agent are prepared using different size fractions of the particles of the same type of gelling agent. These structures are also tested for their equilibrium absorbent capacities in the manner described in the Test Methods section. Furthermore, an effective absorbent capacity of the gelling agent in each structure is also calculated in a manner similar to that described in Example I. A description of the products tested and absorbent capacity results are set forth in Table 1.

TABLE I

| | Effect of Polymeric Gelling Agent (PGA) Particle Size on Equilibrium Absorbent Capacities | | |
|---|---|---|---|
| Structure No. | PGA Particle Size Range (microns) | Structure Absorbent Capacity (grams/gram) | Effective PGA Absorbent Capacity (grams/gram) |
| 1 | 500–710 | 11.5* | 33.3* |
| 2 | 355–500 | 11.2 | 31.3 |
| 3 | 180–250 | 10.6* | 28.5* |
| 4 | 125–180 | 9.9* | 25.0* |
| 5 | 90–125 | 9.7 | 23.8 |

*Average of two determinations

The Table I data indicate that Structures 1 and 2 of the present invention provide both a higher absorbent capacity for the structure and a higher effective absorbent capacity of the gelling agent than do similar structures (Structures 3–5) which utilize generally smaller gelling agent particles.

EXAMPLE III

Absorbent structures similar to that of Examples I and II are prepared using the same components but with varying amounts and sizes of the gelling agent particles in the structures. Absorbent capacities of such structures and effective absorbent capacity of the gelling agent in each such structure are also determined. Such structures and absorbent capacities are described in Table II.

TABLE II

| | Effect of Polymeric Gelling Agent (PGA) concentration | | | |
|---|---|---|---|---|
| Approximate PGA Concentration | Structure Absorbent Capacity (grams/gram) | | Effective PGA Capacity (grams/gram) | |
| (Wt. %) | Large[1] Particles | Small[2] Particles | Large[1] Particles | Small[2] Particles |
| 0 | 6.0* | 6.0* | — | — |
| 10 | 9.3* | 7.9* | 40* | 26* |
| 20 | 11.5* | 9.7 | 33* | 24 |
| 30 | 12.8* | 11.1* | 29* | 24* |

[1]500–710 microns
[2]90–125 microns
*Average of duplicate measurements

The Table II data indicate that the improvement in the effective absorbent capacity of the gelling agent, which improvement is brought about by using larger particle size gelling agent, diminishes as total gelling agent concentration in the structure increases.

EXAMPLE IV

An absorbent structure similar to that described in Example I is prepared using a cross-linked, sodium polyacrylate gelling agent having a gel volume of about 49 grams of synthetic urine per gram and a degree of neutralization of about 70%. The particle-size fraction of such a gelling agent is such that the gelling agent particles pass through a U.S.A. Standard Testing Sieve with 710 micron openings (No. 25 U.S. Series Alternate Sieve Designation) and are retained on a U.S.A. Standard Testing Sieve with 500 micron openings (No. 35 U.S. Series Alternate Sieve Designation). These gelling agent particles are incorporated into the Foley Fluff structure in a concentration of about 15%. The resulting fibrous web has a basis weight of about 0.05 g/cm². This web is then calendered to form a structure which has a density of about 0.19 g/cm³.

EXAMPLE V

The equilibrium absorbent capacity of, and the effective capacity of gelling agent in, the structure of Example IV are compared with those of similar structures wherein smaller particle size fractions of the gelling agent are employed. Results are shown in Table III.

TABLE III

Effect of Polymeric Gelling Agent (PGA) Particle Size Using High Gel Volume PGAs

| Structure No. | PGA Concentration (Wt %) | PGA Particle Size Range (microns) | Structure Absorbent Capacity (grams/gram) | Effective PGA Absorbent Capacity (grams/gram) |
| --- | --- | --- | --- | --- |
| 1 | 15.2* | 500–710 | 12.2* | 46.6* |
| 2 | 14.5 | 355–500 | 12.1 | 48.0 |
| 3 | 14.6 | 180–250 | 11.1 | 41.3 |
| 4 | 13.0 | 125–180 | 10.3 | 39.4 |
| 5 | 14.5 | 90–125 | 10.0 | 33.5 |

*Average of two determinations

The Table III data indicate that, for this relatively high gel volume gelling agent, Structures 1 and 2 of the present invention provide both a higher absorbent capacity for the structure and a higher effective absorbent capacity of the gelling agent than do similar structures (Structures 3–5) which utilize generally smaller gelling agent particles.

EXAMPLE VI

A disposable diaper is prepared using an absorbent structure of the present invention as an absorbent core. The absorbent structure is an hourglass-shaped air-laid mixture comprising 26.6 grams of wood pulp fibers (Foley fluff) and 5 grams of particles of a cross-linked sodium polyacrylate polymeric gelling agent having a gel volume of about 30 grams of synthetic urine per gram and a degree of neutralization of about 70%. Substantially all of the particles of the polymeric gelling agent range in size from about 355–500 microns. Such particles have a mass median particle size of about 430 microns.

The absorbent structure has nonuniform distribution of gelling agent therein such that the weight percent of gelling agent in the front section of the diaper is 20%, in the crotch section of the diaper is 13% and in the back section of the diaper is 12%. Such a structure is calendered to an average density of about 0.15 g/cm³ and has an average basis weight of about 0.05 g/cm².

This hourglass-shaped absorbent structure is utilized as an absorbent core in a diaper prepared in general as described in Buell, U.S. Pat. No. 3,860,003; issued Jan. 14, 1975. In such a diaper, the hourglass core is overwrapped with envelope tissue and inserted between a polypropylene topsheet and a polyethylene backing sheet. Such a diaper structure is especially effective at using the absorbent capacity of the gelling agent in comparison with similar diapers employing smaller particle size fractions of the gelling agent.

What is claimed is:

1. An absorbent structure suitable for use in disposable absorbent articles, said absorbent structure comprising a web formed from a combination of
   A. from about 40% to 95% by weight of the structure of hydrophilic fibers; and
   B. from about 5% to 60% by weight of the structure of nonfibrous, nonfragile particles of hydrogel-forming polymeric gelling agent having an equilibrium gel volume of at least about 20 grams of synthetic urine per gram of gelling agent, said particles having a mass median particle size ranging from about 400 to 700 microns with no more than about 16% by weight of said particles having a particle size less than 200 microns and no more than about 16% by weight of said particles having a particle size greater than 1000 microns, said particles being thoroughly dispersed among said hydrophilic fibers in said web;
   said web having a density of from about 0.06 g/cm³ to 0.3 g/cm³.

2. An absorbent structure according to claim 1 wherein
   A. the hydrophilic fibers are cellulosic fibers comprising from about 70% to 90% by weight of the structure;
   B. the hydrogel-forming polymeric gelling agent comprises from about 10% to 30% by weight of the structure and is a slightly cross-linked, partially neutralized polymer selected from polyacrylates and acrylic acid grafted starch, said gelling agent having an equilibrium extractable polymer content in synthetic urine of no more than about 17% by weight; and
   C. the gelling agent particles have a mass median particle size of from about 410 to 650 microns with no more than about 16% by weight of said particles having a particle size less than 210 microns.

3. An absorbent structure according to claim 2 wherein the gelling agent particles have a mass median particle size ranging from about 420 to 600 microns with no more than about 16% by weight of said particles having a particle size less than 220 microns and no more than about 16% by weight of said particles having a particle size greater than 900 microns.

4. An absorbent structure according to claim 2 wherein the hydrophilic cellulosic fibers are wood pulp fibers and wherein the polymeric gelling agent has a gel volume of from about 25 to 60 grams of synthetic urine per gram of gelling agent.

5. An absorbent structure according to claim 2 wherein the hydrophilic cellulosic fibers are stiffened, twisted, curled cellulose fibers and wherein the polymeric gelling agent has a gel volume of from about 20 to 35 grams of synthetic urine per gram of gelling agent.

6. An absorbent structure according to claim 2 wherein the gelling agent particles have the following size distribution as determined by ASTM analysis on U.S. Sieve Series screens:

| U.S. Sieve Series Alternate Designation | Distribution (Wt %) |
| --- | --- |
| On No. 14 | <0.1 |
| On No. 16 | <1.0 |
| On No. 20 | 10–35 |
| On No. 50 | >50 |
| On No. 100 | <15 |
| Thru No. 100 | ≦5 |

7. A composition especially suitable for use as an absorbent gelling agent in fibrous absorbent web structures, said composition comprising a plurality of nonfibrous, nonfragile particles of a substantially water-insoluble, slightly crosslinked, partially neutralized, hydrogel-forming polymeric gelling agent material wherein;
(A) said polymeric gelling agent material comprises:
(i) from about 50 mole percent to 99.999 mole percent of polymerized unsaturated, polymerizable, acid group-containing monomers; and
(ii) from about 0.001 mole percent to 5 mole percent of a crosslinking agent;
said polymeric gelling agent material having a degree of neutralization of at least about 50% and a gel volume of at least about 20 grams of synthetic urine per gram of gelling agent material; and
(B) said plurality of particles has a mass median particle size ranging from about 400 to 700 microns with no more than about 16% by weight of said particles having a particle size less than 200 microns and no more than about 16% by weight of said particles having a particle size greater than 1000 microns.

8. A composition according to claim 7 wherein
(A) the polymeric gelling agent material is selected from polyacrylates and acrylic acid grafted starch and has an equilibrium extractable polymer content in synthetic urine of no more than about 17% by weight; and
(B) the plurality of gelling agent particles has a mass median particle size ranging from about 410 to 650 microns with no more than about 16% by weight of said particles having a particle size less than 210 microns.

9. A composition according to claim 8 wherein said polymer gelling agent material has a gel volume of from about 25 to 60 grams of synthetic urine per gram of gelling agent and wherein said plurality of gelling agent particles has a mass median particle size ranging from about 420 to 600 microns with no more than about 16% by weight of said particles having a particle size less than 220 microns and no more than about 16% by weight of said particles having a particle size greater than 900 microns.

10. A composition according to claim 8 wherein said plurality of gelling agent particles has the following particle size distribution as determined by ASTM analysis on U.S. Sieve Series screens:

| U.S. Sieve Series Alternate Designation | Distribution (Wt %) |
| --- | --- |
| On No. 14 | <0.1 |
| On No. 16 | <1.0 |
| On No. 20 | 10-35 |
| On No. 50 | >50 |
| On No. 100 | <15 |
| Thru No. 100 | ≦5 |

11. A composition according to claim 8 wherein the gelling agent particles are in the form of agglomerates.

12. An absorbent article of improved absorbency characteristics, said article comprising:
A. a liquid impervious backing sheet;
B. a liquid pervious topsheet; and
C. an absorbent core positioned between said backing sheet and said topsheet, said absorbent core comprising a web formed from a combination of
i) from about 40% to 95% by weight of the web of hydrophilic fibers; and
ii) from about 5% to 60% by weight of the web of nonfibrous, nonfragile particles of hydrogel-forming polymeric gelling agent having an equilibrium gel volume of at least about 20 grams of synthetic urine per gram of gelling agent, said particles having a mass median particle size ranging from about 400 to 700 microns; with no more than about 16% by weight of said particles having a particle size less than 200 microns and no more than about 16% by weight of said particles having a particle size greater than 1000 microns; said particles being thoroughly dispersed among said hydrophilic fibers in said web;
said web having a density of from about 0.06 g/cm$^3$ to 0.3 g/cm$^3$.

13. An absorbent article according to claim 12 wherein,
A. in the web, the hydrophilic fibers are cellulosic fibers comprising from about 70% to 90% by weight of the web;
B. in the web, the hydrogel-forming polymeric gelling agent comprises from about 10% to 30% by weight of the web and is a slightly cross-linked, partially neutralized polymer selected from polyacrylates and acrylic acid grafted starch, said gelling agent having an equilibrium extractable polymer content in synthetic urine of no more than about 17% by weight; and
C. in the web, the gelling agent particles have a mass median particle size ranging from about 410 to 650 microns with no more than about 16% by weight of said particles having a particle size less than 210 microns.

14. An absorbent article according to claim 13 wherein, in the web, the mass median particle size of the polymeric gelling agent particles ranges from about 420 to 600 microns with no more than about 16% by weight of said particles having a particle size less than 220 microns and no more than about 16% by weight of said particles having a particle size greater than 900 microns.

15. An absorbent article according to claim 13 wherein, in the web, the hydrophilic cellulosic fibers are wood pulp fibers and wherein, in the web, the polymeric gelling agent has a gel volume of from about 25 to 60 grams of synthetic urine per gram of gelling agent.

16. An absorbent article according to claim 13 wherein, in the web, the hydrophilic cellulosic fibers are stiffened, twisted, curled cellulose fibers and wherein, in the web, the polymeric gelling agent has a gel volume of from about 20 to 35 grams of synthetic urine per gram of gelling agent.

17. An absorbent article according to claim 13 wherein, in the web, the gelling agent particles have the following particle size distribution as determined by ASTM analysis on U.S. Sieve Series screens:

| U.S. Sieve Series Alternate Designation | Distribution (Wt %) |
| --- | --- |
| On No. 14 | <0.1 |
| On No. 16 | <1.0 |
| On No. 20 | 10-35 |
| On No. 50 | >50 |
| On No. 100 | <15 |
| Thru No. 100 | ≦5 |

18. An absorbent article according to claim 13 wherein
A. said topsheet is coextensive with one face of said core;
B. said backing sheet is coextensive with the face of the core opposite the face covered by said topsheet and has a width greater than that of the core, to thereby provide side marginal portions of the backing sheet which extend beyond the core; and C. said absorbent core is hourglass-shaped.

19. An absorbent article according to claim 18 wherein, within the web in the absorbent core, there is a concentration gradient of polymeric gelling agent particles with the zone of the web nearest the backing sheet having a relatively higher concentration of polymeric gelling agent than the zone of the web nearest the top sheet.

20. An absorbent article according to claim 13 in the form of a sanitary napkin wherein the density of the web in the absorbent core ranges from about 0.09 g/cm$^3$ to 0.22 gm/cm$^3$.

* * * * *